United States Patent [19]

Pyke et al.

[11] 4,415,757

[45] Nov. 15, 1983

[54] PRODUCTION OF SATURATED CARBONYL COMPOUNDS

[75] Inventors: David R. Pyke, Clwyd, Wales; Robert Reid, Warrington, England

[73] Assignee: Imperial Chemical Industries PLC, London, England

[21] Appl. No.: 358,103

[22] Filed: Mar. 15, 1982

[30] Foreign Application Priority Data

Mar. 19, 1981 [GB] United Kingdom ............... 8108709

[51] Int. Cl.³ .......................................... C07C 45/32
[52] U.S. Cl. .................................... 568/475; 568/478
[58] Field of Search ...................... 568/475, 478, 476

[56] References Cited

U.S. PATENT DOCUMENTS 3,637,818 1/1972 Krekeler et al. ................... 568/475

FOREIGN PATENT DOCUMENTS 1213080 11/1970 United Kingdom ............... 568/475
1375329 11/1974 United Kingdom ............... 568/475

*Primary Examiner*—Werren B. Lone
*Attorney, Agent, or Firm*—Cushman, Darby & Cushman

[57] ABSTRACT

A process for the production of a saturated carbonyl compound which comprises bringing into reaction at an elevated temperature in the gas phase an alkane with molecular oxygen and a hydrogen halide in the presence of a solid particulate catalyst composition comprising (1) metallic silver and/or a compound thereof and (2) one or more compounds of at least one other metal having a variable valency.

Useful for the production of acetaldehyde from ethane.

8 Claims, No Drawings

PRODUCTION OF SATURATED CARBONYL COMPOUNDS

The present invention relates to the production of saturated carbonyl compounds by the oxidation of alkanes.

In British Pat. No. 1,213,080 (Lummus Company) there is described a process for producing carbonyl compounds from a feed containing at least one alkane, alkene, cycloalkane, alkyl-substituted aromatic hydrocarbon or alkenyl-substituted hydrocarbons which comprises contacting the feed with an oxygen-containing gas and a melt containing a multivalent metal halide in both its higher and lower valency state to produce an effluent containing a carbonyl compound. Suitable multivalent metal halides include the halides (e.g. chlorides and bromides) of manganese, iron, copper, cobalt and chromium, and the process is preferably carried out using a melt containing a mixture of cuprous and cupric chlorides. In the case of higher melting multivalent metal halides, such as copper chlorides, the melt further includes univalent metal halides, e.g. an alkali metal chloride such as potassium chloride, in order to reduce the melting point of the molten salt mixture. The reaction is carried out within the temperature range 500° F. (260° C.) to 950° F. (510° C.), preferably at temperatures from about 550° F. (286° C.) to about 850° F. (445° C.). For example, the oxidation of propane to propionaldehyde is carried out in a melt comprising cuprous chloride, cupric chloride and potassium chloride at 496° C.

In British Pat. No. 1,375,329 (Lummus Company) there is described a process for producing acetaldehyde which comprises contacting ethane, ethylene, or mixtures thereof with a molten mixture comprising a multivalent metal chloride in both its higher and lower valency state and the corresponding oxychloride at a temperature of 700° F. (371° C.) to 1000° F. (538° C.) in the substantial absence of added chlorine and hydrogen chloride. Suitably the multivalent metal chlorides, and the univalent metal chlorides which may optionally be added to the melt as melting point depressants, are the metal chlorides disclosed in the aforesaid British Pat. No. 1,213,080, e.g. cuprous chloride and cupric chloride as the multivalent chlorides, and an alkali metal chloride such as potassium chloride as the univalent chloride. The molten chloride mixture is preferably oxidised with oxygen to produce an oxychloride containing melt before contacting the melt with ethane and/or ethylene. The preferred reaction temperature is 800° F. (427° C.) to 875° F. (468° C.), for example 825° F. (440° C.) to 850° F. (454° C.) for the oxidation of ethane/ethylene mixtures to acetaldehyde using a melt comprising cuprous chloride/cupric chloride and potassium chloride.

The use of melt processes such as those described in the aforesaid British Patents can give rise to problems connected with the handling of melts and with the necessity to provide suitable materials of construction to minimise corrosion. We have now found certain catalysts which can operate in a temperature regime substantially below that hitherto possible and thus reduce corrosion/erosion problems. In addition the catalysts may be used in the solid particulate state, thus avoiding reactor problems associated with molten salts. This enables both fixed and fluid bed reactors to be employed and minimises problems associated with catalyst volatilisation.

According to the present invention we provide a process for the production of a saturated carbonyl compound which comprises bringing into reaction at an elevated temperature in the gas phase an alkane with molecular oxygen and a hydrogen halide in the presence of a solid particulate catalyst composition comprising (1) metallic silver and/or a compound thereof and (2) one or more compounds of at least one other metal having a variable valency.

The components (1) and (2) comprising the catalyst composition may be present in physical admixture or in chemical combination with one another.

The process of the invention is applicable to a range of alkane starting materials, especially alkanes having 2 to 4 carbon atoms, for example ethane. The starting material may comprise an alkane/alkene mixture. The alkene may be for example, ethylene, propylene and various butenes.

The products of the process typically comprise aldehydes, ketones, acids, alcohols and esters. In general, alkanes produce mainly the corresponding aldehydes, and alkenes when present may produce the corresponding aldehydes or ketones (except for ethylene which produces mainly acetaldehyde).

The process of the invention is especially applicable to the production of acetaldehyde from ethane and ethane/ethylene mixtures.

As already mentioned, the silver may be incorporated into the catalyst composition as metal but it will be appreciated that under the reaction conditions metallic silver may be converted wholly or in part to the halide or oxyhalide corresponding to the halogen of the halogen halide reactant or to the corresponding oxide.

The compounds of silver (component (1) of the catalyst composition) and the compounds of the other metals of variable valency (component (2) of the catalyst composition) which compounds may be the same or different, are suitably present as oxides (which may be converted under the reaction condition to the corresponding halides and/or oxyhalides) and/or halides and/or oxyhalides. Compounds of the catalyst components such as nitrates, carbonates, hydroxides, phosphates and acetates may also be employed which may be converted to oxides, halides, oxyhalides, or mixtures thereof under the reaction conditions. Component (1) and/or component (2) may also be present in the form of a cation exchanged zeolite.

The preferred metals of component (2) are manganese, cobalt, iron, nickel and the platinum group metals (ruthenium, rhodium, palladium, osmium, iridium and platinum) and more particularly manganese or cobalt. Thus a preferred catalyst composition comprises metallic silver and/or silver oxide, halide (e.g. chloride) or oxyhalide (e.g. oxychloride) or mixtures thereof and manganese oxide, halide (e.g. chloride) or oxyhalide or mixtures thereof. Conveniently, the preferred catalyst composition may comprise initially silver oxide and/or metallic silver and manganese oxide, which as already mentioned may at least partially be converted to the corresponding halides and/or oxyhalides under the reaction conditions. In an especially preferred catalyst of silver and manganese, X ray diffraction identified the major phases present before catalytic reaction as silver metal and $AgMn_2O_4$ while for an especially preferred combination of silver and cobalt, the major precursor phase was found to be $AgCoO_2$ (delafossite structure).

It is preferred to employ catalysts having atomic ratios of silver to the other metal or metals of variable valency in the range from 10:1 to 1:10, more preferably between from 3:1 to 1:3, for example 1:1.

The catalyst may conveniently be prepared by coprecipitation of the compounds, e.g. oxides comprising components (1) and (2) which coprecipitation may be effected chemically, thermally or electrically, or by a combination of these methods. Suitably, the coprecipitation consists in preparing a solution containing the materials from which the desired components e.g. oxides can be precipitated. Alternatively the catalysts may be prepared by sintering the components or by combining the molten components.

The catalyst may be supported if desired on known carriers such as, for example, silica, alumina, various zeolites, or titania. The surface area of the support can be varied widely but is usually in the range 0.1 to 50 $m^2/g$.

The supported catalyst may be employed in fixed, moving or fluidised beds of the appropriate size.

The reaction temperature may vary according to the reactant employed. Suitably, for example for the oxidation of ethane or ethane/ethylene, the reaction temperatures are in the range 250° C.–475° C., for example 300° C. to 400° C.

The reaction is normally carried out under atmospheric or superatmospheric pressure, e.g. at a pressure in the range 1 to 100 bars.

The source of oxygen may be oxygen itself or oxygen enriched air. The molar ratios of alkane (and alkene when present) and oxygen are preferably in the range 0.1 to 10 moles of oxygen for each mole of alkane (and alkene), for example 0.5 to 2 moles of oxygen for each mole of alkane (and alkene).

The hydrogen halide is preferably hydrogen chloride. Typically the reaction mixture contains 0.01 to 5 moles of hydrogen halide, for example 0.1 to 0.5 moles of hydrogen halide for each mole of alkane (and alkene.

The products of the reaction may be isolated and used as such or, if desired, may be recycled wholly or partially to the reactor in order to increase the yield of carbonyl compound.

The invention is illustrated by the following Examples.

EXAMPLE 1

A catalyst containing equal atomic proportions of silver and manganese was prepared by coprecipitation from the nitrates. A solution of 17 g of silver nitrate dissolved in 22 ml of water was mixed with 43 ml of 50% manganous nitrate solution and slowly added to a solution of 28 g of NaOH dissolved in 100 ml of water boiling under reflux in a nitrogen atmosphere. Refluxing was continued for 5 hours and after cooling, the black precipitate was filtered off, washed with water until alkali free and then with 25% $NH_4OH$ solution. After further washing until alkali free, the filtrate was dried at 120° C. and heated from 200° C. to 450° C. over a period of 5 hours. Finally the catalyst was calcined for 16 hours at 450° C. At this stage X-ray diffraction showed the product to consist of crystalline $AgMn_2O_4$ and silver metal. After grinding to 250–500 μm mesh size, the catalyst was loaded into a 6.3 mm O.D. tubular microreactor (equipped with an on-line GLC system) to give a bed length of 10 cm. The catalyst was pretreated in a current of hydrogen chloride for one hour at 300° C. Catalytic performance was then assessed under varying gas feed conditions and over a range of temperatures, product analyses being performed by on-line GLC. The results are shown in Table 1, for a reaction temperature of 350° C.

TABLE 1

| Feed Gases mls/min | | | Conversion | Selectivity (%) at 350° C. | | | | | | |
|---|---|---|---|---|---|---|---|---|---|---|
| Air | Ethane | HCl | mol % | MeCHO | EtCl | $C_2H_4$ | $CO_2$ | AcOH | Alcohols | MeCl |
| 12.5 | 2.5 | 0 | 3.3 | 11 | 11 | — | 3 | 34 | 41 | — |
| 12.5 | 2.5 | 0.6 | 12.7 | 42 | 10 | 9 | 12 | 15 | 4 | 4 |
| 25 | 5 | 0.6 | 6.6 | 50.3 | 10 | 12 | 19 | 3 | 9 | 3 |
| 50 | 5 | 0.3 | 5 | 57 | 9 | 6 | 6 | — | 21 | — |

EXAMPLE 2

A silver/cobalt catalyst with silver and cobalt in the atomic proportions of 1:1 was prepared as in Example 1 from silver nitrate and cobaltous nitrate solution.

X-ray diffraction showed the catalyst to contain crystalline $AgCoO_2$.

The following conditions were used:
(a) A feed ratio of ethane:air:hydrogen chloride of 1:5:0.16 (vol). The results obtained for a contact time of 2 seconds are shown in Table 2.
(b) Using different ratios of ethane to HCl in the feed the results obtained at 350° C. and with a contact time of 2 seconds are shown in Table 3.

EXAMPLE 3

A supported silver/manganese catalyst was prepared with silver and manganese in the atomic proportions 1:1 by impregnating a titanium dioxide support (TILCOM E) with saturated silver permanganate solution. After evaporation to dryness the catalyst was calcined for 16 hours at 600° C. The catalyst was tested using a similar procedure to that described in Example 1. The results are shown in Table 4.

TABLE 4

| Temperature | 360° C. | 385° C. |
|---|---|---|
| vol HCl/ethane | 0.15 | 0.10 |
| mol % conversion | 13.8 | 7.0 |
| selectivity acetaldehyde | 71 | 65 |
| $CO_2$ | 6.7 | 15.1 |
| $C_2H_5Cl$ | 11.1 | 7.8 |
| $CH_3Cl$ | 1.3 | 0.6 |
| $C_2H_4$ | 4.6 | 7.1 |
| $CH_2Cl_2$ | 4.4 | 4.2 |

TABLE 2

| Temp (°C.) | Conversion mol (%) | Selectivity (%) | | | | | |
|---|---|---|---|---|---|---|---|
| | | MeCHO | EtCl | MeCl | $CO_2$ | $C_2H_4$ | Acetates |
| 300 | 1.2 | 56 | 25 | — | 19 | — | — |
| 320 | 3.5 | 56 | 26 | 1 | 15 | 3 | — |
| 330 | 6 | 50 | 19 | 1 | 11 | 3 | 7.5 |
| 340 | 7 | 53 | 21 | 1.5 | 14 | 4 | 6 |
| 350 | 8 | 62 | 25 | 1.5 | 20 | 5 | 7 |
| 360 | 11 | 48 | 20 | 1.5 | 19 | 6 | 6 |

TABLE 3

| [HCl]/[Ethane] | Conversion mol (%) | Selectivity (%) at 350° C. | | | | | | |
|---|---|---|---|---|---|---|---|---|
| | | MeCHO | EtCl | MeCl | CO$_2$ | C$_2$H$_4$ | Alcohols | Esters |
| 0.3 | 7.5 | 46 | 28 | 1 | 10 | 5 | 3 | 4 |
| 0.17 | 9 | 46 | 15 | 3 | 7 | 4 | 11 | 14 |
| 0.12 | 8 | 48 | 9 | 7 | 7 | 3 | 10 | 24 |
| 0 | 4 | 54 | 7 | — | — | — | 28 | 9 |

We claim:

1. A process for the production of a saturated carbonyl compound having 2 to 4 carbon atoms which comprises bringing into reaction at a temperature in the range of 250° to 475° C. in the gas phase an alkane having 2 to 4 carbon atoms with molecular oxygen and hydrogen chloride in the presence of a solid particulate catalyst composition comprising (1) metallic silver and/or an oxide, chloride or oxychloride thereof and (2) an oxide, chloride or oxychloride of at least one other metal, selected from manganese, cobalt, iron, nickel and the platinum group metals.

2. A process according to claim 1 wherein the alkane is ethane.

3. A process according to claim 1 or claim 2 wherein the catalyst composition is such that the atomic ratio of silver to the metal or metals of (2) is in the range from 10:1 to 1:10.

4. A process according to claim 3 wherein the atomic ratio of silver to the metal or metals of (2) is in the range from 3:1 to 1:3.

5. A process according to claim 1 or claim 2 wherein the reaction mixture contains from 0.1 to 10 moles of oxygen for each mole of alkane.

6. A process according to claim 5 wherein the reaction mixture contains from the 0.5 to 2 moles of oxygen for each mole of alkane.

7. A process according to claim 1 or claim 2 wherein the reaction mixture contains from 0.01 to 5 moles of hydrogen chloride for each mole of alkane.

8. A process according to claim 7 wherein the reaction mixture contains from 0.1 to 0.5 moles of hydrogen chloride for each mole of alkane.

* * * * *